(12) United States Patent
Mannu et al.

(10) Patent No.: US 12,344,531 B2
(45) Date of Patent: Jul. 1, 2025

(54) SILICA WITH ULTRA-FAST DISSOLUTION PROPERTIES

(71) Applicant: Sil'Innov Srcl, Courcelles (BE)

(72) Inventors: Nicolas Mannu, Waterloo (BE); Quentin Chevrot, La Fare les Oliviers (FR); Karine Croizet-Berger, Court St Etienne (BE); Nicolas Rabasso, Antony (FR); Ivan Coste-Maniere, Grasse (FR); Jullen Estager, Kontich (BE); Benoit Kartheuser, Ciney (BE)

(73) Assignee: Sil'Innov Srcl, Courcelles (BE)

( * ) Notice: Subject to any disclaimer, the term of this patent is extended or adjusted under 35 U.S.C. 154(b) by 175 days.

(21) Appl. No.: 17/754,536

(22) PCT Filed: May 29, 2020

(86) PCT No.: PCT/EP2020/065084
§ 371 (c)(1),
(2) Date: Apr. 5, 2022

(87) PCT Pub. No.: WO2021/069108
PCT Pub. Date: Apr. 15, 2021

(65) Prior Publication Data
US 2024/0059571 A1    Feb. 22, 2024

(30) Foreign Application Priority Data
Oct. 10, 2019    (WO) ................ PCT/EP2019/077458

(51) Int. Cl.
*A61K 33/00*    (2006.01)
*A61K 9/00*    (2006.01)
(Continued)

(52) U.S. Cl.
CPC ............ *C01B 33/18* (2013.01); *A61K 9/0053* (2013.01); *A61K 9/1623* (2013.01); *A61K 33/00* (2013.01);
(Continued)

(58) Field of Classification Search
CPC .............. C01P 2006/14; C01P 2006/16; C01P 2006/90; A23F 5/14; A23L 2/39;
(Continued)

(56) References Cited

U.S. PATENT DOCUMENTS 11,427,476 B2 *    8/2022    Croizet-Berger ...... A61K 8/602
2016/0374943 A1    12/2016    Kucera

FOREIGN PATENT DOCUMENTS

WO    WO-2017182245 A1 *    10/2017    ........... A23L 29/015
WO    2019/166656 A1    9/2019
WO    2021/069108 A1    4/2021

OTHER PUBLICATIONS

Fowler et al. (Adv Mater 2001; 13(9):649-652). (Year: 2001).*
(Continued)

*Primary Examiner* — Ernst V Arnold
(74) *Attorney, Agent, or Firm* — Vorys, Sater, Seymour and Pease LLP

(57) ABSTRACT

Mesoporous silicas with ultra-fast dissolution properties, compositions thereof methods of preparation thereof, and methods of use thereof. Mesoporous silicas with ultra-fast dissolution properties may be prepared by (i) forming a silica comprising an amphiphilic glycoside; and (ii) subsequently subjecting the silica comprising the amphiphilic glycoside to a heat-treatment above 400° C.

15 Claims, 1 Drawing Sheet

(51) Int. Cl.
*A61K 9/16* (2006.01)
*C01B 33/18* (2006.01)

(52) U.S. Cl.
CPC ...... *C01P 2006/14* (2013.01); *C01P 2006/16* (2013.01); *C01P 2006/90* (2013.01)

(58) Field of Classification Search
CPC ...... A23L 29/294; A23L 29/015; A23P 20/10; A23P 20/18; A61K 9/00; A61K 9/0053; A61K 9/1623; A61K 33/00; C01B 33/16
See application file for complete search history.

(56) References Cited

OTHER PUBLICATIONS

Narayan et al. (Pharmaceutics 2018;10(118): 49 pages) (Year: 2018).*
Google translation WO2017182245; 2017:19 pages (Year: 2017).*
ISR-WO dated Aug. 28, 2020 for parent application PCT/EP2020/065084.
Urska Lavrencic Stangar et al., "Alkyl-glycoside surfactants in the synthesis of mesoporous silica films", Silicon Chemistry, Kluwer Academic Publishers, DO,vol. 2, No. 3-4, May 1, 2003 (May 1, 2003), p. 157-165.

* cited by examiner

SILICA WITH ULTRA-FAST DISSOLUTION PROPERTIES

TECHNICAL FIELD

The invention pertains to the technical field of nutraceuticals for providing a bio-resorbable source of silicon to humans or animals.

BACKGROUND

Silicon is an essential trace element in human and animal nutrition. The mechanism and site of action of silicon absorption in the body is well recognized. Silicon plays an important role in connective tissue, especially in bone and cartilage.

EP 2 526 954 describes a silicon complex (I) formed by reacting orthosilicic acid having four free hydroxy groups and at least one stabilizing agent based on phenol or polyphenol, where the free hydroxy groups of orthosilicic acid are stabilized by hydrogen bonding. Such a silicon complex (I) is formulated as a liquid biological preparation, where the liquid biological preparation exhibits a pH of 2-4, the amount of silicon is 0.3-1.4 wt./vol. % and the ratio between the amount of silicon and stabilizing agent is 0.1:1. As such a source of bio-resorbable silicon can be delivered to a subject in liquid form.

WO 2017/182245 provides a mesoporous silica produced by mixing components A and B, wherein A is a surfactant of the family of the saponins and B is a precursor of silica; and a method for the production of said silica.

There remains a need in the art for an improved solid dosage form which allows for enhanced resorption of silicon in the human or animal body. The present invention aims to resolve at least some of the problems mentioned above.

SUMMARY OF THE INVENTION

The present invention provides a mesoporous silica with ultra-fast dissolution properties prepared by (i) forming a mesoporous silica clogged by a tensioactive agent; and (ii) subsequently subjecting said clogged mesoporous silica comprising said tensioactive agent to a heat-treatment above 400° C.

Such silicas were found to dissolve readily when brought into an aqueous environment and consequently release orthosilicic acid, which eventually allows for enhanced resorption in the human or animal body.

In a second aspect, the present invention provides an oral dosage form comprising a mesoporous silica according to the first aspect of the invention. Such an oral dosage form is preferably a tablet. Solid dosage forms are advantageous for ease of administration and dosage to a subject.

In a third aspect, the present invention provides a method for producing a mesoporous silica with ultra-fast dissolution properties, comprising the steps of:
  i. forming a mesoporous silica clogged by a tensioactive agent; and
  ii. subsequently subjecting said mesoporous silica clogged by said tensioactive agent to a heat-treatment above 400° C.

In a fourth aspect, the present invention provides in a use of a mesoporous silica according to the first aspect of the invention in nutrition or food supplements for humans or animals, cosmetics or pharmaceuticals.

DETAILED DESCRIPTION OF THE INVENTION

Figure 1:
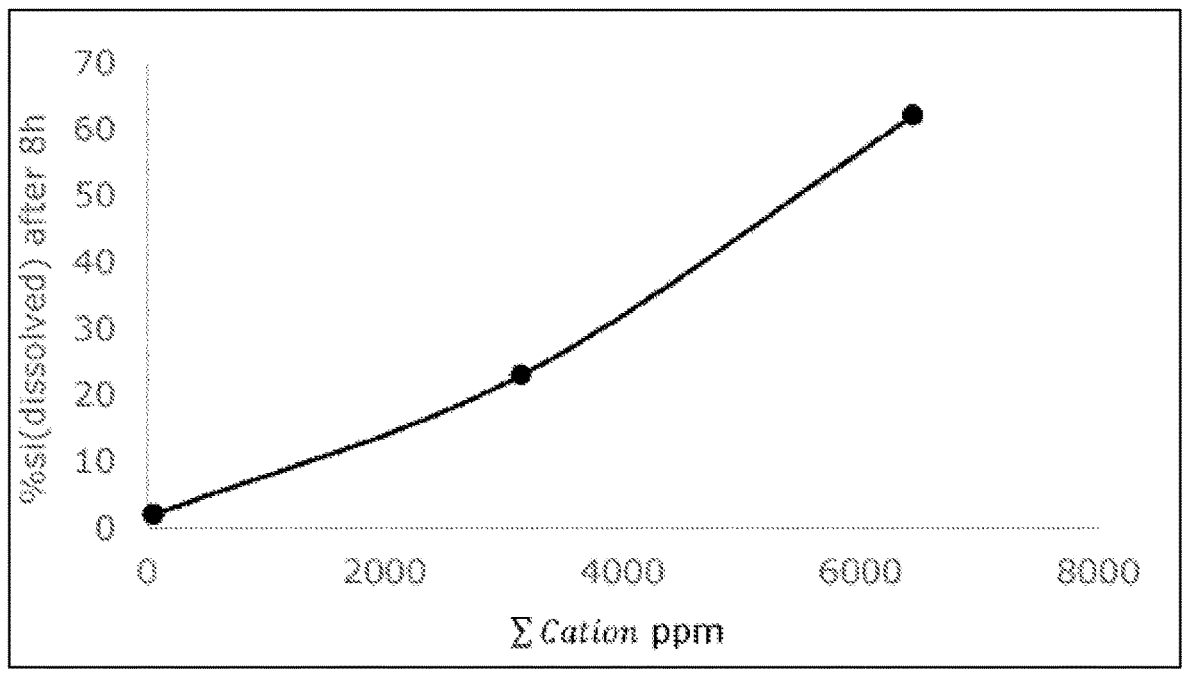
FIG. 1 shows the dissolution rate of mesoporous silica in function of the initial cationic load of the saponin-water mixture used in the production of said mesoporous silica.

The present invention concerns mesoporous silica for silicium uptake by humans or animals.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

The expression "% by weight", "weight percent", "% wt." or "wt. %", here and throughout the description unless otherwise defined, refers to the relative weight of the respective component based on the overall weight of the formulation.

In a first aspect, the invention provides a mesoporous silica with ultra-fast dissolution properties prepared by (i) forming a mesoporous silica clogged by a tensioactive agent; and (ii) subsequently subjecting said mesoporous silica clogged by said tensioactive agent to a heat-treatment above 400° C.

This provides an alternative mesoporous silica compared to silica according to the prior art, e.g. as described in WO 2017/182245.

Moreover and very surprisingly, the inventors found that the thus obtained mesoporous silica shows unexpectedly high dissolution rates in terms of the dissolution of the silica in aqueous environments, thereby releasing high quantities of silicic acid $Si(OH)_4$ in reasonably short times—thereby providing an effective source of bio-available silicium. This is supported by the results depicted in Table 3 and as discussed further.

A "clogged mesoporous silica" as used herein refers to a mesoporous silica comprising a tensioactive agent within at least some of its mesopores. A "clogged" mesoporous silica" is not restricted to a mesoporous silica in which all or almost all mesopores are clogged. Without being bound by theory, it is believed that the tensioactive agent comprised within the mesoporous silica partially clogs those mesopores. That is to say, the mesopores are at least in part blocked or otherwise unavailable. It should be noticed that this "clogging" does not require all pores, or even all mesopores, to be unavailable. Additionally, the pores do not need to be clogged permanently. In fact, the clogging is believed to be reversible, that is to say the mesopores can be unclogged. For example, the mesopores may at least partially be unclogged by example washing out said tensioactive agent.

In a preferred embodiment, the present invention provides in a mesoporous silica according to the first aspect of the invention, whereby said clogged mesoporous silica is subjected to a heat-treatment between 450° C. and 950° C. More preferably, said clogged mesoporous silica is subjected to a heat-treatment between 450° C. and 700° C., and even more preferably between 500° C. and 600° C. Most preferably, said clogged mesoporous silica is subjected to a heat-treatment at 500° C., 510° C., 520° C., 530° C., 540° C., 550° C., 560° C., 570° C., 580° C., 590° C. or 600° C.

In a preferred embodiment, the present invention provides in a mesoporous silica according to the first aspect of the invention, whereby said tensioactive agent is an amphiphilic glycoside. In another preferred embodiment, the present invention provides in a mesoporous silica according to the first aspect of the invention, whereby said tensioactive agent is an amphiphilic glycoside in combination with fatty acid esters. Amphiphilic glycosides, alone or in combination with fatty acid esters (such as the commercial "Tween" products), were found to be especially preferred over other tensioactive agents as this class of compounds rather efficiently is subjected to calcination at the temperatures indicated above.

An amphiphilic compound is a chemical compound possessing both hydrophilic and hydrophobic or lipophilic properties. Such a compound is called amphiphilic or amphipathic. This forms the basis for a number of areas of research in chemistry and biochemistry. Common amphiphilic substances are also designated as tensioactive agents or substances, soaps, detergents and lipoproteins.

The hydrophobic group is typically a large hydrocarbon moiety, such as a long chain of the form of an alkyl group $CH_3(CH_2)_n$, with n>4.

The hydrophilic group falls into one of the following categories:
1. Charged groups, comprising anionic and cationic groups. Anionic groups may be carboxylates, sulfates, sulfonates, or phosphates. Cationic groups may be ammonium.
2. Polar, uncharged groups, most notably alcohols and polyalcohols, such as diacyl glycerol (DAG), sugar alcohols, and oligoethyleneglycols with long alkyl chains.

When placed in an immiscible biphasic system consisting of aqueous and organic solvents, the amphiphilic compound will partition the two phases. The extent of the hydrophobic and hydrophilic portions determines the extent of partitioning.

Preferred amphiphilic compounds include many biological compounds such as but not limited to: phospholipids, cholesterol, glycolipids, fatty acids, saponins, etc. Especially preferred amphiphilic compounds are glycosides.

A glycoside is a molecule in which a sugar is bound to another functional group via a glycosidic bond. In formal terms, a glycoside is any molecule in which a sugar group is bonded through its anomeric carbon to another group via a glycosidic bond. Glycosides can be linked by an O- (an O-glycoside), N- (a glycosylamine), S- (a thioglycoside), or C- (a C-glycoside) glycosidic bond. According to the IUPAC, the name "C-glycoside" is a misnomer; the preferred term is "C-glycosyl compound". By preference, the sugar is bonded to a non-sugar for the molecule to qualify as a glycoside, thus excluding polysaccharides. The sugar group is then known as the glycone and the non-sugar group as the aglycone or Benin part of the glycoside. The glycone can consist of a single sugar group (monosaccharide) or several sugar groups (disaccharide or oligosaccharide).

Glycosides may be classified according to the chemical nature of the aglycone and comprise alcoholic glycosides such as salicin, anthraquinone glycosides which contain an aglycone group that is a derivative of anthraquinone, coumarin glycosides wherein the aglycone is coumarin or a derivative such as apterin, chromone glycosides wherein the aglycone is called benzo-gamma-pyrone, cyanogenic glycosides wherein the aglycone contains a cyanohydrin group, flavonoid glycosides wherein the aglycone is a flavonoid such as hesperidin, naringin, rutin and quercitrin, phenolic glycosides wherein the aglycone is a simple phenolic structure such as arbutin, saponins, steroidal glycosides or cardiac glycosides wherein the aglycone part is a steroidal nucleus, steviol glycosides found in the *Stevia* plant and having steviol as the aglycone part, iridoid glycosides which contain an iridoid group such as aucubin, Geniposidic acid, theviridoside, loganin, catalpol, and thioglycosides which contain sulfur such as sinigrin and sinalbin.

In a more preferred embodiment, the present invention provides in a mesoporous silica according to the first aspect of the invention, whereby said amphiphilic glycoside is saponin. Saponins are a class of chemical compounds found in particular abundance in various plant species. More specifically, they are amphipathic glycosides grouped phenomenologically by the soap-like foam they produce when shaken in aqueous solutions, and structurally by having one or more hydrophilic glycoside moieties combined with a lipophilic triterpene derivative.

The most important sources of saponins used in the food and cosmetics industry are the *Quillaja saponaria* Molina tree, the *Yucca schidigera*, the Southeast Asian shrub *Camellia sinensis*, known as the tea plant and the leaves of *Hedera helix* L., known as the Ivy leaf. The inventors have discovered that the cooperative self-assembly mechanism can be achieved in the presence of natural saponin-type surfactants. It appears that, as in the case of "conventional" industrial surfactants, the saponins aggregate to form, with the silica precursor, a hybrid phase on which the synthesis of mesoporous material will occur.

The saponins used in the context of this invention are triterpenoid glycosides whose main structure (I) aglycone (sapogenin) can take the following forms: dammarenediols (dammaranes), cucurbitadienol (cucurbitanes), hopanol (hopanes), lanosterols (lanostanes), tirucalladienol (tirucallanes), β-amyrin (oleananes), oo-amyrin (ursanes), taraxasterols (taraxasteranes), lupeol (lupans).

Methyl radicals, carboxylic functions, aldehyde or alcohol; hydrogen atoms, hydroxyl groups; as well as simple or branched osidic chains are also attached to the aglycone backbone. Within the osidic chains, the following sugars are preferred: D-glucose, L-rhamnose, D-galactose, D-glucuronic acid, L-arabinose, D-xylose, D-fructose, D-adipose, D-fucose. In the case where the aglycone comprises an osidic chain, one will speak of monodesmoside and in the case where two chains of glycosides are linked to the skeleton aglycone one will speak of bidesmoside. In a preferred embodiment, the saponin used has the following oleanane structure according to Structure (I) below such that R1 and R4 are methyl groups, R2 is a hydrogen atom and R3 is a carboxylic group.

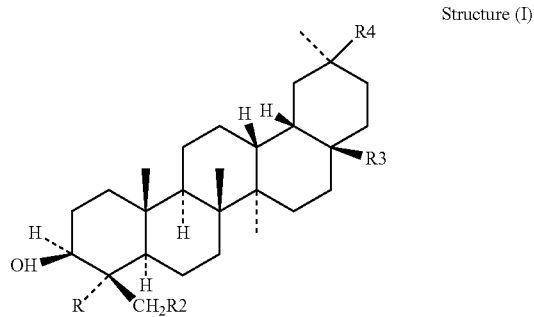

Structure (I)

According to another advantageous embodiment, the structuring agent contains one or more of the following saponins: saponin 1, saponin 2, saponin 3, saponin 4, saponin 5, saponin 6, saponin 6, saponin 7, saponin 8, saponin 9, saponin 10, saponin 19, saponin 20a, saponin 20b, saponin 21a, saponin 21b, saponin 22a, saponin 22b, saponin 23, saponin S7, saponin S8, saponin S9, saponin S10, saponin SU, saponin S12, *Quillaja* saponin 7, 17, 18, 21 (also referred to as QA-7, QA-17, QA-18, QA-21).

According to one embodiment of the invention, the saponins used have a main steroidal aglycone structure of spirostanol or furostanol type or a steroidal glycoalkaloid structure of spirosolane or solanidane type.

In a preferred embodiment, the present invention provides in a mesoporous silica according to the first aspect of the invention, whereby said amphiphilic glycoside is food grade. This is advantageous to allow for consumption of the obtained silica by humans and/or animals. Thus, a safe and bioavailable source of silicium is provided.

In a preferred embodiment, the present invention provides in a mesoporous silica according to the first aspect of the invention, whereby said clogged mesoporous silica is formed by (i-a) mixing a silica precursor in presence of said tensioactive agent and (i-b) subsequently granulating. In a more preferred embodiment, the clogged mesoporous silica which is eventually subjected to the heat-treatment process is a clogged mesoporous silica comprising at least 20% by weight of tensioactive agent, more specifically amphiphilic glycoside, e.g. saponin, relative to the weight of the clogged mesoporous silica, preferably between 20 and 80% by weight and more advantageously between 35 and 60% by weight of said clogged mesoporous silica. Most preferably, the clogged mesoporous silica is a mesoporous silica comprising 35 wt. %, 37 wt. %, 39 wt. %, 41 wt. %, 43 wt. %, 45 wt. %, 47 wt. %, 49 wt. %, 51 wt. %, 53 wt. %, 55 wt. %, 57 wt. %, 59 wt. % or 61 wt. % of tensioactive agent. Said weight of the clogged mesoporous silica refers to the sum of the weight of the silica and the tensioactive agent.

In a preferred embodiment, the present invention provides in a mesoporous silica according to the first aspect of the invention, whereby said mesoporous silica has mesopores having an average pore size of at least 2 nm. In a preferred embodiment, the silica comprises mesopores whose minimum average diameter is 1 nm. The pore diameter was calculated from nitrogen sorption isotherms at liquid nitrogen temperature (77K) according to the method of Barrett, Joyner and Halenda (BJH). The diameter of the mesopores of silica, established from the isotherm of nitrogen sorption at 77K, is 2, 3, 4, 5, 6, 7, 8, 9, 10, 11, 12, 13, 14, 15, 16, 17, 18, 19, 20, 21, 22, 23, 24 or 25 nm or any value between the above values.

In a preferred embodiment, the present invention provides in a mesoporous silica according to the first aspect of the invention, having a silica surface area, calculated from nitrogen sorption isotherms at liquid nitrogen temperature (77K) by the Brunauer, Emmett and Teller (BET) theory, of at least 20 m$^2$/g, 40 m$^2$/g, 50 m$^2$/g, or 60 m$^2$/g. The specific surface is at most 800 m$^2$/g, 900 m$^2$/g, 1000 m$^2$/g or 1500 m$^2$/g or any value between the aforementioned values.

In a preferred embodiment, the present invention provides in a mesoporous silica according to the first aspect of the invention, whereby said silica has a porous volume of at least 0.1 cm$^3$/g. In a preferred embodiment, the pore volume of the silica was calculated from nitrogen sorption isotherms at liquid nitrogen temperature (77K) by the method of Barrett, Joyner and Halenda (BJH). Said pore volume is at least 0.1 cm$^3$/g, 0.2 cm$^3$/g, 0.4 cm$^3$/g, 0.5 cm$^3$/g and at most 0.6 cm$^3$/g, 0.8 cm$^3$/g, 1.0 cm$^3$/g, 1.2 cm$^3$/g, 1.5 cm$^3$/g or any value included between the above values.

In a preferred embodiment, the present invention provides in a mesoporous silica according to the first aspect of the invention, whereby said silica precursor is represented by the formula Si(OR1)(OR2)(OR3)(OR4) or R1-Si(OR2)(OR3)(OR4) whereby R1, R2, R3 and R4 are independently selected from hydroxyl, alkyl, glycols, trimethyl-1,2,3,4-tetrahydronaphthalene, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxy-bis(trimethylsilyloxy)silyl, methyl-bis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy)silyl, 4,7,7-trimethyl-3-bicyclo[2.2.1]heptanyl, 2,2,4-trimethyl-3-bicyclo[2.2.1]heptanyl, propan-2-yloxy-bis(trimethylsilyloxy)silyl, dibutoxy(trimethylsilyloxy)silyl, trimethyl trimethoxysilyl, dibutoxy(ethenyl)silyl, diethyl bis(trimethylsilyl), (butan-2-yloxy)silyl, diacetyloxy-[(2-methylpropan-2-yl)oxy]silyl, acetyloxy(diethoxy)silyl, 4-(dimethylamino)phenyl, 4-(dimethylamino)phenyl, 2-(diethylamino)ethyl, pyridin-3-yl, 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-methoxyethoxy)ethyl, 2-butoxyethyl, 2-ethoxyethyl, 2-methoxyethyl, acetyl, acetyloxy(dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate or trihydroxysilyloxy; or by the formula xSiO$_2$:M$_y$O whereby M is one or more metal atoms, one or more transition metal atoms, one or more non-metals, or ammonium, and whereby y=1, 2, 3 or 4 and x is the ratio of SiO$_2$/M$_y$O.

In a preferred embodiment, the present invention provides in a mesoporous silica according to the first aspect of the invention, whereby R1, R2, R3 and R4 are independently selected from methyl, ethyl, propyl and butyl, preferably from methyl or ethyl, and whereby preferably R1, R2, R3 and R4 are equal. It is preferred that all O—R bonds be hydrolyzable. The preferred silica precursor of formula $Si(OR)_4$ is tetraethyl orthosilicate and/or tetramethyl orthosilicate. According to one embodiment of the invention, the silica precursor is represented by the formula $xSiO_2/M_yO$ where M is one or more metal atoms, one or more transition metal atoms, one or more non-metal atoms, a methylammonium, actinide, y=1 or 2 or 3 or 4 and x is the $SiO_2/M_yO$ molar ratio. The metal atom can be alkaline (y=2) or alkaline earth (y=1). The silica precursor of formula $xSiO_2/M_yO$ may be chosen from the group comprising orthosilicate, sodium, potassium or calcium metasilicate.

In a preferred embodiment, the present invention provides in a mesoporous silica according to the first aspect of the invention, whereby said clogged mesoporous silica comprising a tensioactive agent is formed by mixing a silica precursor in presence of said tensioactive agent at a pH between 8 and 13, preferably between 9 and 11 and most preferably at a pH of about 9, 10 or 11. Preferably, said pH is attained by addition of a suitable base to an aqueous solution comprising said tensioactive agent, i.e. amphiphilic glycoside. More preferably, said base is ammonium hydroxide.

In a second aspect, the present invention provides an oral dosage form comprising a mesoporous silica according to the first aspect of the invention. Preferably, said oral dosage form is a solid oral dosage form such as a tablet or a powder, and more preferably said solid oral dosage form is a tablet. For reasons of ease in dissolution behaviour, said tablet is not provided with an additional coating.

In a preferred embodiment, the present invention provides an oral dosage form according to the second aspect of the invention, comprising said silica in an amount of at least 1 wt. %, relative to the total weight of said oral dosage form, preferably at least 25 wt. %. In a more preferred embodiment, the present invention provides an oral dosage form according to the second aspect of the invention, comprising said silica in an amount of at least 50 wt. %, preferably at least 80 wt. %. A higher percentage of the silica according to the invention allows for higher concentration of silicium in the gastro-intestinal tract of the subject, and thus allows for better uptake in the human or animal body.

In a preferred embodiment, the clogged mesoporous silica further comprises alkali or earth alkaline metal ions. More preferably, said tensioactive agent can comprise or be complexed with alkali or earth alkaline metal ions. Most preferably, said amphipathic glycoside has polar moieties. These polar moieties may be alkali or earth alkaline metal ions. More preferably, alkali and earth alkaline metal ions can be introduced into a solution of amphipathic glycosides. Suitable alkali metal ions are $Li^+$, $Na^+$ and $K^+$. Suitable alkaline earth metals are $Ca^{2+}$, $Mg^{2+}$ and $Sr^{2+}$. Preferred alkali and earth alkaline metals are $Na^+$, $K^+$, $Ca^{2+}$ and $Mg^{2+}$. This is due to the biological effects of lithium and strontium ions, even in low quantities.

In a particularly preferred embodiment, the invention relates to a mesoporous silica prepared by (i) forming a clogged mesoporous silica comprising an amphiphilic glycoside and a cationic load, wherein said cationic load consists of cations chosen from the list of $Na^+$, $K^+$, $Ca^{2+}$ and $Mg^{2+}$; and (ii) subsequently subjecting said clogged mesoporous silica comprising said amphiphilic glycoside to a heat-treatment above 400° C.

It is believed that the polar moieties of said amphipathic glycosides and the earth alkaline metal ions will stabilize one another. The mixture of alkali and/or earth alkaline metal ions and amphipathic glycosides can then be employed for the formation of mesoporous silica according to the present invention.

The cationic load is defined herein as the sum of the molar concentrations of alkali and earth alkaline metal ions. The dissolution rate of the mesoporous silica was surprisingly found to be directly related to the cationic load of the clogged mesoporous silica comprising an amphiphilic glycoside and a cationic load of alkali and earth alkaline metal ions prior to the heat-treatment.

In a further aspect, the present invention provides a solid food product comprising a mesoporous silica according to the first aspect of the invention, further comprising one or more of the following ingredients: oxygen sensitive edible oils; minerals; oxygen sensitive fats including dairy fats; oil soluble ingredients; vitamins; fragrances or aromas; flavours; enzymes; probiotic bacteria; prebiotics; nutraceuticals; amino acids; herbal extracts; herbs; plant extracts; edible acids; salt; antioxidants.

Oxygen Sensitive Edible Oils

Oxygen sensitive edible oils include polyunsaturated fatty acids which themselves include canola oil, borage oil, evening primrose oil, safflower oil, sunflower oil, pumpkinseed oil, rosemary oil, rice bran oil, flaxseed oil, wheatgerm oil, grapeseed oil, linseed oil. Some of these oils contribute linoleic acid, alpha-linoleic acid, oleic acid, palmitic acid, stearic acid. Also included are marine oils, for example, those derived from fish such as tuna, herring, mackerel, sardine, cod liver and shark.

Minerals and Trace Elements

Suitable minerals include: macrominerals comprising Ca, P, Mg, Na, K; microminerals comprising Fe, Zn, Cu, Se, Cr, I, Mn, Mo, F. Suitable trace elements include Ni, V, B, Co.

The blending and compression of particular metal powders with silicon powder may be used to create edible microbatteries. Following ingestion, the gastro-intestinal fluid acts as an electrolyte. If the metal is less noble than silicon then the resulting galvanic coupling increases the dissolution of that metal resulting in increased bioavailability.

Vitamins

Suitable vitamins include Ascorbic Acid, Beta-carotene, Biotin, Choline, Folic Acid, Niacin, Pantothenic Acid (Vitamin B5), Phylloquinone (Vitamin K), Pyridoxine (Vitamin B6), Riboflavin (Vitamin B2), Thiamin (Vitamin B1), Vitamin A, Vitamin B12, Vitamin D, Vitamin E and mixtures thereof. The vitamin and silicon may be combined by allowing the vitamin to impregnate the silicon, optionally in the presence of gentle heat, typically in the range of 40° C. and 200° C.

Fragrances, Aromas and Flavours

Suitable fragrances, aromas and flavours are non-toxic and suitable for foodstuffs and will be readily apparent to the skilled person, see Bauer et al, "Common Fragrances & Flavours", Wiley, 1997, pp 278. Preferred fragrances, aromas and flavours are "Generally Recognised As Safe" (GRAS) by the FDA. Alcohols, aldehydes, ketones, esters and lactones are classes of compounds most frequently used in natural and artificial fragrances.

More specifically, suitable flavours (or flavouring agents) include: one or more of spice oleoresins derived from allspice, basil, capsicum, cinnamon, cloves, cumin, dill, garlic, marjoram, nutmeg, paprika, black pepper, rosemary and tumeric; essential oils such as anise oil, caraway oil, clove oil, eucalyptus oil, fennel oil, garlic oil, ginger oil, peppermint oil, onion oil, pepper oil, rosemary oil, spearmint oil; citrus oils including orange oil, lemon oil, bitter orange oil and tangerine oil; alliaceous flavours which include garlic, leek, chive, and onion; botanical extracts such as arnica flower extract, chamomile flower extract, hops extract, and marigold extract; botanical flavour extracts such as blackberry, chicory root, cocoa, coffee, kola, liquorice root, rose hips, sarsaparilla root, sassafras bark, tamarind and vanilla extracts; protein hydrolysates such as hydrolyzed vegetable protein (HVP's), meat protein hydrolyzates, milk protein hydrolyzates; natural and artificial compounded flavours which include those disclosed in S. Heath, Source Book of Flavours, Avi Publishing Co., Westport, Conn., 1981, p. 149-277. Particular flavour compounds are, for example: benzaldehyde, diacetyl (2,3-butanedione), vanillin, ethyl vanillin and citral (3,7-dimethyl-2,6-octadienal). The flavouring agent may be in the form of an oil, aqueous solution, non-aqueous solution or an emulsion. Flavour essences, i.e. the water soluble fraction derived from fruit or citrus can be utilized, and typically at lower levels than the ingredients mentioned above.

Preferred food aromas (or aromatising agents) include food aromas for liquid food products, particularly instant soups and beverages such as coffee. Other suitable food aromas include those used in desserts such as instant puddings, and frozen food products such as frozen pizza. The food aromas may also be those suitable for use in food which needs to be reconstituted with hot water or milk or heated by the consumer prior to consumption. Suitable food aromas include the following: cheese aroma; aromas for hot soluble coffee-based beverages such as coffee, hazelnut, amaretto, chocolate, cream and vanilla; aromas for hot soluble tea-based beverages such as raspberry, cream and vanilla; aromas for hot cocoa-based beverages such as raspberry, amaretto, cream, chocolate and vanilla; aromas for hot soups such as mushroom, tomato, beef and chicken; aromas for beverages such as coffee, tea, cherry, grape, and strawberry; aromas for dessert products such as raspberry, chocolate, butterscotch, cherry, grape, strawberry, banana, and vanilla; aromas for other products such as cream, seafood, meat, garlic and onion. The aroma flavour may be part of an aromatizing composition which may optionally also include one or more other constituents such as a non-volatile edible fat or oil, a surfactant, a wetting agent, a foaming agent, an extremely volatile solvent, a propellant, dissolved edible solids, an antioxidant, or an aroma precursor.

The production of dehydrated food compositions often involves processing conditions such as elevated temperature, which often causes loss of desirable food aroma. One known technique of overcoming such loss is to add additional aroma and flavour to dehydrated foodstuffs and beverages. Such aromas and flavours are usually complex, comprising many organoleptically active compounds, which combine to create the characterizing aroma of the product. Since aromas and flavours are often extremely powerful and unstable in their undiluted state, they are combined with a carrier to render them more stable and easier to handle. The carriers are preferably neutral or complementary in organoleptic impact and do not contribute to the characterizing aroma of the product. Desirable characteristics of carriers for liquid systems include blandness and miscibility with other liquid carriers and with liquid aromas. Traditional carriers include ethanol, propylene glycol, glycerol, vegetable oil, benzyl alcohol, triacetin, tripropionin, triethyl citrate, and tributyrin.

Natural essential oils from botanical sources are typically intensely flavoured and naturally aromatic due to their inherent volatility. This makes them an ideal choice as aromatizing constituents for use in the manufacture of food products. Unfortunately, volatile essential oils do not exist in all food sources used to manufacture food products. In addition, essential oils that do occur naturally in some foods are often not sufficiently abundant or readily extracted to permit their economical use in processed foods, and some are not approved for food use.

The use of silicon according to the present invention provides one or more of the following attributes: high density to ensure aroma released from floating not submerged particles; non-toxic nature with full or partial biodegradability into silicic acid; non-oily nature thereby avoiding undesirable "slick" on drink surface; hydrophobicity and nanoscale porosity.

Enzymes

Suitable enzymes are selected from the classes of carbohydrases, pectic enzymes, celluloses, proteases, oxidases, and lipases. Examples include amylase, bromelain, catalase, ficin, glucoamylase, glucose isomerase, glucose oxidase, invertase, lactase, lipase, papain, pepsin, pullulanase and rennet.

Probiotic Bacteria

Probiotics are dietary supplements containing potentially beneficial microorganisms or bacteria. More specifically, probiotic refers to microorganisms that form at least a part of the transient or endogenous flora and thereby exhibit a beneficial prophylactic and/or therapeutic effect on the host organism. The prophylactic and/or therapeutic effect of a lactic acid-producing bacteria suitable for use in the present invention may result, in part, from a competitive inhibition of the growth of pathogens due to one or more of the following: (i) superior colonization abilities; (ii) parasitism of undesirable microorganisms; (iii) the production of lactic acid and/or other extracellular products possessing antimicrobial activity. A probiotic bacteria which is suitable for use in the present invention may advantageously possess one or more of the following characteristics: (i) the ability to produce lactic acid; (ii) beneficial function within the gastrointestinal tract; (iii) non-pathogenic. Lactic acid production markedly decreases the pH (i.e., increases acidity) within the local micro-floral environment and does not contribute to the growth of many undesirable, physiologically-deleterious bacteria and fungi. Thus, by the mechanism of lactic acid production, the probiotic inhibits growth of competing pathogenic bacteria. Typical lactic acid-producing bacteria which are useful as probiotics in the present invention include efficient lactic acid producers such as non-pathogenic members of the *Bacillus* genus which produce bacteriocins or other compounds which inhibit the growth of pathogenic organisms. Exemplary lactic acid-producing, non-pathogenic *Bacillus* species include, but are not limited to: *Bacillus coagulans; Bacillus coagulans* Hammer; and *Bacillus brevis* subspecies *coagulans*.

Examples of lactic acid-producing *Lactobacillus* species include, but are not limited to: *Lactobacillus acidophilus, Lactobacillus casei, Lactobacillus* DDS-1, *Lactobacillus GG, Lactobacillus rhamnosus, Lactobacillus plantarum, Lactobacillus reuteri, Lactobacillus gasserii, Lactobacillus jensenii, Lactobacillus delbruekii, Lactobacillus, bulgaricus, Lactobacillus salivarius* and *Lactobacillus sporogenes* (also designated as *Bacillus coagulans*). Exemplary lactic acid-producing Sporolactobacillus species include all Sporolactobacillus species, for example, Sporolactobacillus P44.

Examples of lactic acid-producing *Bifidiobacterium* species include, but are not limited to: *Bifidiobacterium adolescentis, Bifidiobacterium animalis, Bifidiobacterium bifidum, Bifidiobacterium bifidus, Bifidiobacterium breve,*

*Bifidiobacterium infantis, Bifidiobacterium infantus, Bifidiobacterium longum*, and any genetic variants thereof.

The *Bacillus* species, particularly those species having the ability to form spores (e.g., *Bacillus coagulans*), are preferred for use in the present invention. The ability to sporulate makes these bacterial species relatively resistant to heat and other conditions, provides for a long shelf-life in product formulations, and is ideal for survival and colonization of tissues under conditions of pH, salinity, and the like within the gastrointestinal tract. Moreover, additional useful properties of many *Bacillus* species include being non-pathogenic, aerobic, facultative and heterotrophic, thus rendering these bacterial species safe and able to readily colonize the gastrointestinal tract.

Prebiotics

A prebiotic is a natural or synthetic substance that supports the growth of and/or nurtures probiotics. More specifically the prebiotic is a non-digestible food ingredient that beneficially affects the host by selectively stimulating the growth and/or activity of one or a limited number of bacteria in the colon. They are typically carbohydrates of relatively short length. Examples are the inulin-type fructans such as lactulose and inulin.

Nutraceuticals

A nutraceutical ingredient provides medical or health benefits, including the prevention and treatment of disease. In general, a nutraceutical is specifically adapted to confer a particular health benefit on the consumer. Suitable nutraceuticals for use in the present invention may be selected from Aloe Vera (*Aloe ferox, A. barbadensis*), Artichoke, Asian Ginseng (*Panax ginseng*), Astragalus, Bee Pollen, Bilberry (*Vaccinium myrtillus*), Black Cohosh, *Capsicum*-Cayenne, Hot Pepper (*Capsicum* species), Cascara Sagrada (*Rhamnus purshiana*), Cat's Claw (*Uncaria tomentosa*), Chamomile (*Matricaria recutita*), Cranberry, Dandelion (*Taraxacum officinale*), Donq Quai (*Angelica sinensis*), Echinacea (*Echinacea purpurea* and related species), Evening Primrose Oil (*Oenothera biennis*), Feverfew (*Tanacetum parthenium*), Fructo-oligosaccharides, Garlic (*Allium sativum*), Ginger (*Zingiber officinale*), *Ginkgo* (*Ginkgo biloba*), Ginseng, Glucarate, Glucosamine, Goldenseal (*Hydrastis canadensis*), Gotu Kola (*Centella Asiatica*), Grape Seed Extract, Green Tea, Guarana (Paullinacupana), Hawthorne (*Crataegus oxyacantha*), Inositol, Inulin, Isoflavones, Kava Kava (*Piper methysticum*), L-carnitine, Lecithin, Licorice (*Glycyrrhiza glabra* and *G. uralensis*), Lycopene, Milk Thistle (*Silybum marianum*), Mod. Citrus Peel, Nettles, Oligofructose, Omega-3s, *Passiflora*, Passion Flower (*Passiflora incarnata*), Pau d'Arco, (*Tabebuia impetiginosa*), Peppermint (*Mentha piperita*), Phospholipids, Polyphenol, *Psyllium* (*Plantago ovata* and P. Major), Pycnogenol, Queroetin D-Ilmonene; Reishi, Ribonucleic Acid, Royal Jelly, St. John's Wort (*Hypericum perforatum*), Saw Palmetto (*Serenoa repens; Sabal serrulata*), Schisandra, Soybean Isoflavones, Tumeric Valerian (*Valeriana officinalis*) and mixtures thereof.

Amino Acids

Suitable amino acids for use in the present invention may be selected from Alanine, Arginine, Aspartic Acid, Asparagine, Carnitine, Cysteine, Cystine, Glutamic Acid, Glutamine, Glutathione, Glycine, Histidine, Isoleucine, Leucine, Lysine, Methionine, Ornithine, Phenylalanine, Proline, Serine, Taurine, Threonine, Tryptophan, Tyrosine, Valine and mixtures thereof.

Plant Extracts and Herbs

Suitable plant extracts include one or more plant sterols, these include beta-sitosterol, campesterol, stigmasterol. Suitable plant stanols include sitostanol, octacosanol, policosanol.

Suitable Herbs Include Black Walnut, Burdock, Chamomile, Comfrey,

*Echinacea*, eucalyptus, hawthorn, hyssop, *Ginkgo*, hyssop, lemon balm, milk thistle, mullein, peppermint, *Psyllium*, sage, saw palmetto, sheep sorrel, slippery elm, St John's Wort, thyme, turkey rhubarb, valerian, vitex.

Herbs suitable for use for medicinal purposes are described in The Natural Pharmacy by M. Polunin & C. Robbins (Dorling Kindersley 1999), 144 pp. In particular, pages 30-131 list suitable herbs. Suitable culinary herbs are described in Food Commodities, 2nd Edition pp 158-163 by B. Davis (Butterworth Heinemann 1994).

Edible Acids

Suitable edible acids for use in the present invention may be selected from citric acid, ascorbic acid, malonic acid, acetic acid, tartaric acid, sorbic acid, fumaric acid, malic acid, phosphoric acid, succinic acid and nicotinic acid.

Antioxidants

Suitable antioxidants for use in the present invention may be selected from sodium carbonate, calcium carbonate, butylated hydroxyanisole (BHA), butylated hydroxytoluene (BHT), lecithins, sodium lactate, calcium lactate, calcium malate and ammonium citrate.

Food Preparation

Methods for incorporating the silicon into food are numerous. Suitable mixing equipment for use in the present invention is diverse and includes, for example, screw mixers, ribbon mixers and pan mixers. Other examples include high speed propeller or paddle mixers for liquid food or beverages; tumble mixers for dry powders; Z-blade mixers for doughs and pastes. Suitable grinding machines include hammer, disc, pin and ball millers. Extrusion is an important very high throughput (about 300-9000 kg/hr) technique for mixing and providing shape to foodstuffs and is suitable for use in the present invention. Cold and hot extruders may be used.

These can be single or twin screw. Extruded foods include cereals, pasta, sausages, sugar or protein based products.

The ingredient may be combined with the silicon prior and/or during and/or after the mixing process.

The ingredient or ingredients may be loaded onto and/or into the silicon in various ways. For example, the one or more ingredients may be deposited onto the surface of the silicon particles, incorporated into the pores of porous silicon, incorporated into the pores formed by the agglomeration or consolidation of silicon particles (particularly nanoparticles) or bound or otherwise associated with the surface of the silicon. For example, the silicon may be used, in effect to coat or partially coat one or more ingredients. In particular, the silicon may be used to coat or partially coat breakfast cereals or a product or products suitable for making beverages, such as coffee granules, coffee powder, tea, cocoa powder, chocolate powder. Suitable methods for loading the ingredient with the silicon include the techniques of pan coating, fluidised bed, spray drying, spray chilling, enrobing, dusting/breading, coextrusion. Of these physical methods, spray drying of a silicon suspension is preferred. These are all well-known techniques, details of which may be found in standard texts, for example, for a number of these techniques see Food Processing Technology, Principles and Practice by P J Fellows, second edition, Woodhead Publishing Ltd.

The ingredient to be loaded with the silicon may be dissolved or suspended in a suitable solvent, and silicon particles may be incubated in the resulting solution for a suitable period of time. Both aqueous and non-aqueous slips have been produced from ground silicon powder and the processing and properties of silicon suspensions have been studied and reported by Sacks in Ceram. Eng. Sci. Proc., 6, 1985, p. 1109-23 and Kerkar in 3. Am. Chem. Soc. 73, 1990, p. 2879-85. The removal of solvent will result in the ingredient being deposited on the surface of the silicon particles. However, if the particles comprise porous silicon, or agglomerated or consolidated particles (for example, agglomerated or consolidated nanoparticles) of silicon the solution of the ingredient will penetrate into the pores of the silicon by capillary action, and, following solvent removal, the ingredient will be present in the pores. Preferred solvents are water, ethanol, and isopropyl alcohol, GRAS solvents and volatile liquids amenable to freeze drying.

Higher levels of loading, for example, at least about 15 wt. % of the loaded ingredient based on the loaded weight of the silicon may be achieved by performing the impregnation at an elevated temperature. For example, loading may be carried out at a temperature which is at or above the melting point of the ingredient to be loaded. Quantification of gross loading may conveniently be achieved by a number of known analytical methods, including gravimetric, EDX (energy-dispersive analysis by x-rays), Fourier transform infra-red (FTIR), Raman spectroscopy, UV spectrophotometry, titrimetric analysis, HPLC or mass spectrometry. If required, quantification of the uniformity of loading may be achieved by techniques that are capable of spatial resolution such as cross-sectional EDX, Auger depth profiling, micro-Raman and micro-FTIR.

The loading levels can be determined by dividing the weight of the ingredient taken up during loading (equivalent to the mass of the ingredient taken up divided by its density) by the void volume of the porous silicon prior to loading multiplied by one hundred. The total quantity of silicon present in the food according to the present invention, may be about 0.01 to 50 wt. %, preferably from about 0.01 to 20 wt. % and even more preferably 0.1 to 5 wt. %.

In a third aspect, the present invention provides a method for producing a mesoporous silica with ultra-fast dissolution properties, comprising the steps of:
 i. forming a clogged mesoporous silica comprising a tensioactive agent; and
 ii. subsequently subjecting said clogged mesoporous silica comprising said tensioactive agent to a heat-treatment above 400° C.

In a more preferred embodiment, the method comprises the steps of:
 i. forming a clogged mesoporous silica comprising a tensioactive agent and a cationic load, wherein said cationic load consists of cations chosen from the list of $Na^+$, $K^+$, $Ca^{2+}$ and $Mg^{2+}$; and
 ii. subsequently subjecting said clogged mesoporous silica comprising said tensioactive agent to a heat-treatment above 400° C.

In a further particularly advantageous embodiment, the method provides a mesoporous silica with ultra-fast dissolution properties, wherein the dissolution rate of the mesoporous silica can be tuned by varying the cationic load employed in step i. The inventors have surprisingly found that increasing the cationic load will almost linearly increase the dissolution rate of the resulting mesoporous silica. The tensioactive agent and the cationic load may be produced through ion-exchange.

In a further preferred embodiment, the molar concentration of alkali and earth alkaline metal ions with respect to the total mixture of amphipathic glycosides and alkali and/or earth alkaline metal ions is at least 10 ppm, more preferably at least 20 ppm, more preferably at least 30 ppm, more preferably at least 40 ppm, more preferably at least 50 ppm, more preferably at least 100 ppm, more preferably at least 250 ppm, most preferably at least 500 ppm. In another preferred embodiment, the molar concentration of alkali and earth alkaline metal ions with respect to the total mixture of amphipathic glycosides and alkali and/or earth alkaline metal ions is at most 50000 ppm, more preferably at most 40000 ppm, more preferably at most 30000 ppm, more preferably at most 20000 ppm, more preferably at most 15000 ppm, more preferably at most 10000 ppm, more preferably at most 9000 ppm, most preferably at most 8000 ppm.

Furthermore, the cationic load can be varied in order to obtain a desired dissolution rate. This provides an easy method to design a mesoporous silica suitable as drug delivery system, wherein the dissolution rate and therefor the drug release rate can be easily adjusted.

In a preferred embodiment, the molar concentration of alkali and earth alkaline metal ions with respect to the total mixture of amphipathic glycosides and cationic load of alkali and/or earth alkaline metal ions is varied between 10 ppm and 50000 ppm, more preferably the molar concentration is varied between 20 ppm and 40000 ppm, more preferably the molar concentration is varied between 30 ppm and 30000 ppm, more preferably the molar concentration is varied between 40 ppm and 20000 ppm, more preferably the molar concentration is varied between 50 ppm and 10000 ppm, more preferably the molar concentration is varied between 100 ppm and 9000 ppm, more preferably the molar concentration is varied between 200 ppm and 8000 ppm, most preferably the molar concentration is varied between 500 ppm and 8000 ppm.

In a preferred embodiment, the tensioactive agent is added to the solvent, preferably water, in an amount sufficient to obtain a micellar concentration of between 0.1 and 1000 times the critical micelle concentration (CMC). Preferably, the tensioactive agent is added to the solvent in an amount sufficient to obtain a micellar concentration of between 10 and 900 times, 20 and 800 times, 30 and 700 times, 40 and 600 times, 50 and 500 times, 60 and 400 times, and 300 times, 80 and 200 times, 90 and 100 times the critical micellar concentration or any value between the aforementioned values.

In a preferred embodiment, the silica precursor is added to the solvent in a quantity sufficient so that the ratio between the amount of silica precursor and the amount of tensioactive agent is between 0.1 and 50. The silica precursor is preferably added dropwise to the solvent.

In a preferred embodiment, the temperature of the solution obtained following the addition of the silica precursor to the solvent is maintained between 15° C. and 35° C., preferably between 20° C. and 25° C. The pH of the surfactant solution is at least 7. The solution can have an alkaline pH which is obtained by the addition of suitable solutions and/or molecules such as ammonium hydroxide. The pH of the solvent may be 8, 9, 10, 11, 12 or 13 or any value between the above values. The pH of the solution is preferably 9.5.

In a preferred embodiment, the mixture of silica precursor in the solvent is subsequently left under stirring for at least 5 hours and at most 24 hours at a minimum temperature of about 20° C., this incubation time is followed by a filtration step allowing a solid clogged mesoporous silica comprising mesoporous silica and tensioactive agent to be obtained. The stirring of the mixture can also be followed by evaporation of the mixture thus obtaining a solid clogged mesoporous silica comprising mesoporous silica and tensioactive agent.

The clogged mesoporous silica is not washed before further processing but may be subjected to at least one drying step, preferably under reduced pressure of 0.1 to mmHg.

In a most preferred embodiment, the method for producing the mesoporous silica comprises the following steps:

- introducing saponins into water at pH of about 10 in an amount necessary and sufficient to obtain a micellar concentration of between 0.1 and 1000, preferably between 1 and 1000 times the CMC (critical micellar concentration);
- dissolving the saponins by stirring the solution at a temperature between 15° C. and 35° C.;
- dropwise addition of a silica precursor, i.e. triethoxysilane, under stirring such that the ratio between the amount of silica precursor and the amount of saponin is between 0.5 and 50, preferably between 1 and 50;
- aging of the mixture under stirring for a period of time ranging from 10 to 100 hours and preferably from 10 to 20 hours at a temperature of between and 70° C.;
- filtration of the aged product;
- optionally, drying the product under reduced pressure; and
- heating the (dried and) aged product to a temperature of about 550° C. for a period of 2 hours.

In one especially preferred embodiment, the precursor-surfactant mixture, is aspirated at the spray dryer and is pushed through a two-fluid or ultrasonic nozzle having an orifice of 0.15 to 1.2 mm to generate droplets of about 20 μm. The column inlet temperature is between 120 and 250° C. and preferably between 140 and 180° C. A flow of air with a power of less than 1 m 3 that a suitable temperature at the top of the column allows, 1) the evaporation of the aqueous solvent, 2) the self-assembly of the micelles of surfactant and 3) the condensation of the silica precursor.

In a fourth aspect, the present invention provides in a use of a mesoporous silica according to the first aspect of the invention in nutrition or food supplements for humans or animals, cosmetics or pharmaceuticals.

Examples 1-6 and Comparative Examples 1-6

The invention is further described by the following non-limiting examples which further illustrate the invention, and are not intended to, nor should they be interpreted to, limit the scope of the invention.

Preparation

In a reactor, under agitation, saponin solution is added to water and pH is adjusted to 10 with adequate quantity of NH$_4$OH. Triethoxysilane (TEOS) is then added with a peristaltic pump at a rate of 1.8 g/min and the formulation is aged under agitation for 24 hours. The amounts of tetraethoxysilane, saponin, water and ammonium hydroxide used for the preparation of mesoporous silica according to Examples 1 to 6 and Comparative Examples 1 to 6 is summarized in Table 1.

TABLE 1

Amounts of tetraethoxysilane, saponin, water and ammonium hydroxide used for the preparation of mesoporous silica.

| Example | tetraethoxy silane (g) | saponin (g) | water (g) | NH$_4$OH (g) |
|---|---|---|---|---|
| Ex. 1 | 9.94 | 13.24 | 325.92 | 0.9 |
| Ex. 2 | 19.9 | 26.48 | 651.82 | 1.8 |
| Ex. 3 | 9.94 | 13.24 | 325.92 | 0.9 |
| Ex. 4 | 28400 | 50100 | 919200 | 2300 |
| Ex. 5 | 25.56 | 45.09 | 827.3 | 2.07 |
| Ex. 6 | 25.56 | 45.09 | 827.3 | 2.07 |
| Comp. Ex. 1 | 17.04 | 22.72 | 559.8 | 0.44 |
| Comp. Ex. 2 | 39.8 | 52.96 | 1303.64 | 3.6 |
| Comp. Ex. 3 | 19.9 | 26.48 | 651.82 | 1.8 |
| Comp. Ex. 4 | 39.8 | 52.96 | 1303.64 | 3.6 |
| Comp. Ex. 5 | 39.76 | 79.48 | 1277.2 | 3.56 |
| Comp. Ex. 6 | 39.76 | 79.48 | 1277.2 | 3.56 |

The formulation is sprayed under the conditions presented in Table 2 and a clogged mesoporous silica comprising silica and saponin is collected as a powder.

TABLE 2

Spray conditions.

| T ° in | 140° C. |
|---|---|
| Inlet gaz flow | 0.3 m$^3$/min |
| Pressure drop cyclone (AP) | 60 mbar |
| Nozzle Bi-fluid | 0.4 mm |
| Nozzle air flow | 7 l/min |
| Nozzle air | 0.6 bar |
| Spray rate | 6.0 g/min |

The powder obtained after spray drying of the mixtures according to Examples 1 to 6 is calcined at 550° C. for 2 hours.

The powder obtained after spray drying of the mixtures according to Comparative Examples 1, 2 and 5 is washed and subsequently calcined at 550° C. for 2 hours. The powder obtained after spray drying of the mixtures according to Comparative Examples 3, 4 and 6 is washed and not calcined.

Dissolution Tests

The dissolution method is as followed. 100 mg of silica powder is placed in 900 mL of water in a type II USP dissolution apparatus. Samples are taken at different times and filtered with a 0.45 μm nylon membrane. The Si concentration is determined either by ICP-OES (total Si content) or by molybdate complexation (monomeric Si). The results of the two dosages were the same for every tested sample.

The silicon dissolution percentages after 6 hours in water are presented in Table 3. The results clearly show that the mesoporous silica according to the invention show a distinctly higher dissolution compared to mesoporous silica known in the art.

TABLE 3

Amount of Si dissolved in water, as a weight percent of the amount of Si in the mesoporous silica.

| Example | wt. % Si dissolved |
|---|---|
| Ex. 1 | 31.2 |
| Ex. 2 | 28.76 |
| Ex. 3 | 11.01 |
| Ex. 4 | 49.06 |

TABLE 3-continued

Amount of Si dissolved in water, as a weight percent
of the amount of Si in the mesoporous silica.

| Example | wt. % Si dissolved |
|---|---|
| Ex. 5 | 43.08 |
| Ex. 6 | 46.74 |
| Comp. Ex. 1 | 3.69 |
| Comp. Ex. 2 | 4.94 |
| Comp. Ex. 3 | 1.42 |
| Comp. Ex. 4 | 2.25 |
| Comp. Ex. 5 | 9.55 |
| Comp. Ex. 6 | 3.21 |

Examples 7-11: Influence of Cations on the Dissolution Rate

In a beaker, 22.5 grams of saponin-water mixture (15 w % saponin in water) is introduced. Approximately 850 grams of additional water are added, and the resulting mixture is kept under vigorous agitation with a magnetic stirrer set at 550 rpm for 2 minutes. Approximately 1.2 grams of a 25 w % ammonium hydroxide solution is added until a pH of 9.5 is reached. After 5 minutes of stirring at 550 rpm, 25.6 grams of TEOS is added dropwise via a peristaltic pump. The rate of addition is set at 1.76 g/min.

TABLE 4 summary of the formulation.

| Products | Weight (g) | % w |
|---|---|---|
| Saponin mixture | 22.5 | 2.50 |
| TEOS | 25.6 | 2.84 |
| NH$_4$OH | 1.2 | 0.13 |
| Water | 850 | 94.4 |

The mixture is kept under agitation (550 rpm) at room temperature for 24 h before being spray dried.

The spray drying process is performed with the settings below on ProCept 4M8Trix spray-dryer.

TABLE 5 parameters of the spray drying process

| Temperature inlet gaz | 140° C. |
|---|---|
| Inlet gaz flow | 0.3 m$^3$/min |
| Cyclone air flow | 47 L/min |
| Cyclone | Medium |
| Nozzle | Bi-fluid-0.4 mm |
| Nozzle air flow | 7 l/min |
| Spray rate | 6.0 g/min |

The powder recovered after spray-drying is calcinated in order to remove the organic template. The heat treatment parameters are as follows: From ambient temperature to 500° C. with a heat rate ramp of 10° C./min. The product stays 2 hours at 500° C. before being taken off at this temperature.

Table 6 below summarizes the cations identified and their concentrations for six batches of saponin mixture, measured by ICP-OES:

TABLE 6

Concentration of alkali and earth alkaline cations in the saponin mixture

| Example | Ca (ppm) | K (ppm) | Mg (ppm) | Na (ppm) | Cationic load (ppm) |
|---|---|---|---|---|---|
| Example 7 | 1866 | 2183 | 686 | 3235 | 7970 |
| Example 8 | 1906 | 2216 | 694 | 3277 | 8093 |
| Example 9 | 1140 | 3574 | 1119 | 614 | 6446 |

The cationic load in this example is expressed as the sum of the molar concentrations of the alkali and earth alkali cations detected and quantified by ICP-OES in ppm. These concentrations are with respect to the cation-saponin mixture. It does not include the silica-based material and thus is not representative of the concentrations in the final mesoporous silica product.

The cations identified and quantified in the saponin mixture such as sodium, potassium, magnesium, and calcium form inorganic compounds during the spray drying step. These compounds are not eliminated during the heat treatment process at 500° C.

The concentrations of alkali and earth alkali cations of the saponin mixture can be modified by a demineralization process. For that, the saponin water solution is treated by an ion exchange resin (Dowex® MB Mixed) with supplies H$^+$/OH$^-$ ions.

Using this process of demineralization, we have obtained
a completely demineralized saponin (example 11)
a 50% demineralized saponin by mixing the completely demineralized and the non-demineralized saponins (example 10)

TABLE 7

The concentration of the alkali and earth alkaline metals in the saponin mixture as measured by ICP-OES before and after treatment:

| Example | Demineralization (%) | Ca (ppm) | K (ppm) | Mg (ppm) | Na (ppm) | Cationic load (ppm) |
|---|---|---|---|---|---|---|
| Example 9 | 0 | 1140 | 3574 | 1119 | 614 | 6446 |
| Example 10 | 50 | 563 | 1693 | 555 | 333 | 3143 |
| Example 11 | 99.2 | 23 | 0 | 13 | 19 | 55 |

The rate of demineralization expressed in percent is determined by the ratio between the cationic load after and before the demineralization treatment of Saponin-water mixture.

Using these 3 batches of saponin mixture with differing degree of demineralization, three mesoporous silica's have been produced (examples 9, 10 and 11 in table 7.) We have consequently analyzed the dissolution properties thereof.

The dissolution rate of the mesoporous silica-based materials is expressed in a percentage of silicium dissolved in water after 8 hours of test. The dissolution test is performed at 37° C. in ultra-pure water in a Sotax® apparatus. The dissolution rates measured from samples of examples 9, 10 and 11 in function of the initial cationic load of the Saponin-water mixture are represented in FIG. 1.

It is clear that the dissolution properties are linked to the cationic load present in the saponin-water mixture used during the synthesis process. When the cationic load increases, the dissolution rate of silicium increases. This allows the present process to be used to optimize the dissolution rate of a mesoporous silica.

FIG. 1: Dissolution rate of mesoporous silica in function of the initial cationic load of the saponin-water mixture used in the production of said mesoporous silica.

Figure 2:
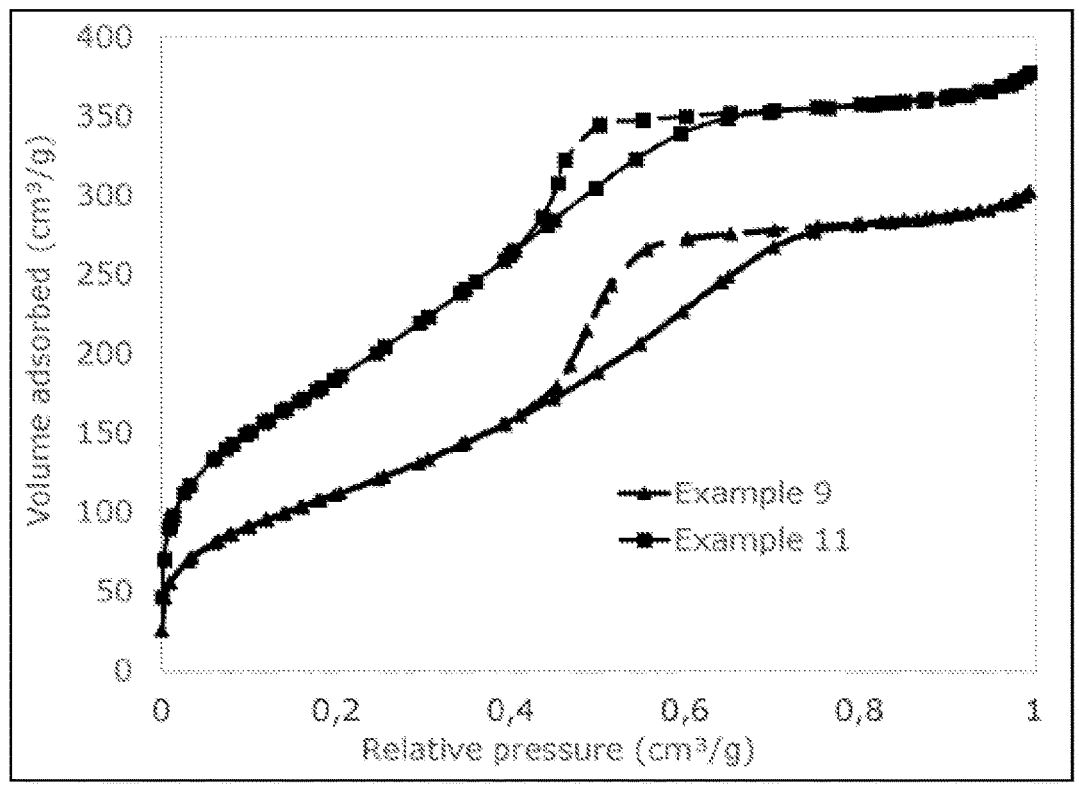
FIG. 2 shows BET sorption isotherm of examples 9 and 11, volume absorbed ($cm^3/g$) in function of relative pressure ($cm^3/g$).

The porosity of the silica-based materials obtained from the examples 9 and 11 have been analyzed by BET method and the sorption isotherm are represented in FIG. 2.

Example 11 has a specific surface area $S_s$ of 417 m²/g, an maximum absorbed volume of 0.49 cm³/g and an estimated pore diameter of 4.3 nm.

Example 11 has a specific surface area $S_s$ of 696 m²/g, an maximum absorbed volume of 0.55 cm³/g and an estimated pore diameter of 3.3 nm.

The cationic load in Saponin-water mixture influences the specific surface area and pore volume of the final silica material. When the cationic load of the saponin at the beginning of the synthesis process increases the specific surface area and the pore volume decrease.

FIG. 2: BET sorption isotherm of examples 9 and 11, Volume absorbed (cm³/g) in function of relative pressure (cm³/g).

The invention claimed is:

1. A mesoporous silica prepared by:
   (i) forming a clogged mesoporous silica comprising an amphiphilic glycoside and a cationic load of alkali and/or earth alkaline metal ions,
      wherein step (i) further comprises (i-a) mixing a silica precursor in presence of said amphiphilic glycoside at a pH between 8 and 13, and (i-b) subsequently filtrating or drying said mixture,
      wherein said amphiphilic glycoside is present at 35% by weight to 80% by weight, based on the total weight of said silica precursor and said amphiphilic glycoside; and
   (ii) without washing said clogged mesoporous silica prior to further processing, subsequently subjecting said clogged mesoporous silica comprising said amphiphilic glycoside to a heat-treatment above 400° C.

2. The mesoporous silica according to claim 1, whereby said silica clogged mesoporous is subjected to a heat-treatment between 450° C. and 950° C.

3. The mesoporous silica according to claim 1, whereby said amphiphilic glycoside is saponin.

4. The mesoporous silica according to claim 1, wherein said cationic load consists of cations chosen from the list of $Na^+$, $K^+$, $Ca^{2+}$ and $Mg^{2+}$.

5. The mesoporous silica according to claim 1, wherein, in step (i), the molar concentration of said alkali and/or earth alkaline metal ions, with respect to the total mixture of said amphiphilic glycoside and said alkali and/or earth alkaline metal ions, is 10 ppm to 50,000 ppm.

6. The mesoporous silica according to claim 1, whereby said silica has mesopores having an average pore size of at least 1 nm.

7. The mesoporous silica according to claim 1 whereby said silica has a porous volume of at least 0.1 cm³/g.

8. The mesoporous silica according to claim 5, whereby said silica precursor is represented by the formula Si(ORI)(OR2)(OR3)(OR4) or RI—Si(OR2)(OR3)(OR4) whereby RI, R2, R3 and R4 are independently selected from hydroxyl, alkyl, glycols, trimethyl-1, 2, 3, 4-tetrahydronaphthalene, 1,1,1,3,3,3-hexafluoropropan-2-yl, dimethylsilyl, trimethylsilyl, ethoxysilyl, tributoxysilyl, diethoxy(methoxy)silyl, trimethoxysilyl, ethoxy(dimethoxy)silyl, butoxy(dipropoxy)silyl, tripropoxysilyl, diethoxy(trimethylsilyloxy)silyl, ethoxy-bis(trimethylsilyloxy)silyl, methyl-bis(trimethylsilyloxy)silyl, butoxy-bis(trimethylsilyloxy)silyl, diethoxy(triethoxysilyloxy)silyl, dimethyl(vinyl)silyl, trimethylsilyloxy, (3-methylpentoxy)silyl, 4,7,7-trimethyl-3-bicyclo[2.2. I] heptanyl, 2,2,4-trimethyl-3-bicyclo[2.2. I] heptanyl, propan-2-yloxy-bis(trimethylsilyloxy) silyl, dibutoxy (trimethylsilyloxy)silyl, trimethyl trimethoxysilyl, dibutoxy (ethenyl)silyl, diethyl bis(trimethylsilyl), (butan-2-yloxy) silyl, diacetyloxy-[(2-methylpropan-2-yl)oxy]silyl, acetyloxy(diethoxy)silyl, 4-(dimethylamino)phenyl, 4-(dimethylamino)phenyl, 2-(diethylamino)ethyl, pyridin-3-yl, 2-methylpropan-2-yl)oxy, 2,2,3,3,4,4,5,5,6,6,7,7-dodecafluoroheptyl, trichloro-2-ethylbutoxy, cyclononyl, 1-methoxypropan-2-yl, 2-(2-methoxyethoxy)ethyl, 2-butoxyethyl, 2-ethoxyethyl, 2-methoxyethyl, acetyl, acetyloxy (dipropoxy)silyl, 5-methyl-2-propan-2-ylcyclohexyl, butan-2-yloxy, methylphenyl, cyclohexyl, 2-aminoethyl, phenyl, prop-2-enyl, 2-fluoroethyl, acetate or trihydroxysilyloxy; or by the formula $xSiO2:MyO$ whereby M is one or more metal atoms, one or more transition metal atoms, one or more non-metals, or ammonium, and whereby y=1, 2, 3 or 4 and x is the ratio of $SiO2/MyO$.

9. The mesoporous silica according to claim 8, whereby R1, R2, R3 and R4 are independently selected from methyl, ethyl, propyl and butyl.

10. An oral dosage form comprising a mesoporous silica prepared by:
   (i) forming a clogged mesoporous silica comprising an amphiphilic glycoside and a cationic load of alkali and/or earth alkaline metal ions,
      wherein step (i) further comprises (i-a) mixing a silica precursor in presence of said amphiphilic glycoside at a pH between 8 and 13, and (i-b) subsequently filtrating or drying said mixture,
      wherein said amphiphilic glycoside is present at 35% by weight to 80% by weight, based on the total weight of said silica precursor and said amphiphilic glycoside; and
   (ii) without washing said clogged mesoporous silica prior to further processing, subsequently subjecting said clogged mesoporous silica comprising said amphiphilic glycoside to a heat-treatment above 400° C.

11. The oral dosage form according to claim 10, comprising said silica in an amount of at least 1 wt. %, relative to the total weight of said oral dosage form.

12. The oral dosage form according to claim 11, comprising said silica in an amount of at least 50% by weight.

13. A method for producing a mesoporous silica, comprising the steps of:
   (i) forming a clogged mesoporous silica comprising an amphiphilic glycoside and a cationic load of alkali and/or earth alkaline metal ions,
      wherein step (i) further comprises (i-a) mixing a silica precursor in presence of said amphiphilic glycoside at a pH between 8 and 13, and (i-b) subsequently filtrating or drying said mixture,
      wherein said amphiphilic glycoside is present at 35% by weight to 80% by weight, based on the total weight of said silica precursor and said amphiphilic glycoside; and
   (ii) without washing said clogged mesoporous silica prior to further processing, subsequently subjecting said clogged mesoporous silica comprising said amphiphilic glycoside to a heat-treatment above 400° C.

14. A composition comprising a mesoporous silica according to claim 1, wherein the composition is selected from the group consisting of nutrition supplements, food supplements, cosmetics, and pharmaceuticals.

15. The method of claim 13, wherein, prior to step (i-a), the method further comprises varying the molar concentration of said alkali and/or earth alkaline metal ions, with respect to the total mixture of said amphiphilic glycoside and said alkali and/or earth alkaline metal ions, from 10 ppm to 50,000 ppm.

* * * * *